US008288166B2

(12) United States Patent
Dahint et al.

(10) Patent No.: US 8,288,166 B2
(45) Date of Patent: Oct. 16, 2012

(54) SENSOR CHIP WITH CONNECTED NON-METALLIC PARTICLES COMPRISING A METALLIC COATING

(75) Inventors: Reiner Dahint, Eppelheim (DE); Petra Bücker, Heidelberg (DE); Elka Trivela, Sofia (BG); Sören Schilp, Mannheim (DE); Michael Himmelhaus, Kodaira (JP); Hatice Acunman, Neckargerach (DE)

(73) Assignee: Fujirebio Inc., Tokyo (JP)

( * ) Notice: Subject to any disclaimer, the term of this patent is extended or adjusted under 35 U.S.C. 154(b) by 530 days.

(21) Appl. No.: 11/918,944

(22) PCT Filed: Apr. 21, 2006

(86) PCT No.: PCT/EP2006/003714
§ 371 (c)(1),
(2), (4) Date: May 15, 2008

(87) PCT Pub. No.: WO2006/111414
PCT Pub. Date: Oct. 26, 2006

(65) Prior Publication Data
US 2009/0073447 A1    Mar. 19, 2009

(30) Foreign Application Priority Data

Apr. 22, 2005  (EP) .................................. 05008931

(51) Int. Cl.
*G01N 21/03*    (2006.01)
(52) U.S. Cl. ........................................ 436/165; 436/172
(58) Field of Classification Search .................. 436/165, 436/172; 422/82.05, 425, 551; 356/445; 250/458.1
See application file for complete search history.

(56) References Cited

U.S. PATENT DOCUMENTS

| 6,331,276 | B1 * | 12/2001 | Takei et al. ................ 422/82.09 |
| 6,685,986 | B2 * | 2/2004 | Oldenburg et al. ........... 427/214 |
| 2001/0002315 | A1 * | 5/2001 | Schultz et al. ................ 436/172 |
| 2005/0018274 | A1 | 1/2005 | Halas et al. |

(Continued)

FOREIGN PATENT DOCUMENTS

EP    0965835 A2    12/1999

(Continued)

OTHER PUBLICATIONS

Himmelhaus M, et al., "Cap-shaped gold nanoparticles for an optical biosensor", Sensors and Actuators B., Elsevier Sequoia S.A., Lausanne, CH, Apr. 2000, pp. 24-30, vol. 63, No. 1-2, XP004195042, ISSN: 0925-4005.

(Continued)

*Primary Examiner* — Jill Warden
*Assistant Examiner* — Dwan A Gerido
(74) *Attorney, Agent, or Firm* — Sughrue Mion, PLLC

(57) ABSTRACT

The invention provides a chip comprising a substrate with at least one surface and a layer of particles having a non-metallic core and a coating made of a metal or a metal alloy, characterized in that each non-metallic core, on average, forms a metal-surrounded contact point with at least one other non-metallic core and/or the substrate surface.
The invention also provides a method for preparing a chip, comprising the steps of,
  adsorbing non-metallic particles on said surface of the substrate, and, subsequently,
  adsorbing colloids of a metal on said non-metallic particles to provide the shell made of a metal or a metal alloy, and a chip which is obtainable by said method.
The chip can be employed in optical devices for the detection of analytes.

18 Claims, 9 Drawing Sheets

U.S. PATENT DOCUMENTS

2009/0302235 A1* 12/2009 Himmelhaus ............ 250/458.1

FOREIGN PATENT DOCUMENTS

| JP | 11001703 A | 1/1999 |
| JP | 11326193 A | 11/1999 |
| JP | 2003247936 A | 9/2003 |
| JP | 2005144569 A | 6/2005 |

OTHER PUBLICATIONS

Himmelhaus, et al., "Cap-Shaped Gold Nanoparticles for an Optical Biosensor," Sensors and Actuators B (2000) pp. 24-30.

Amarie D., et al., "Submicrometer Cavity Surface Plasmon Sensors," J. Phys. Chem. B., vol. 109, Aug. 18, 2005, pp. 15515-15519 (whole document).

Japanese Office Action corresponding to Japanese Patent Application No. 2008-50717, mailed Aug. 9, 2011. English language translation.

R. Horie, et al., Gold-Coated Opal Films As Refractive Index Sensors. English language translation.

Japanese Office Action corresponding to Japanese Patent Application No. 2008-507017, dated Mar. 8, 2012. English language translation.

* cited by examiner a) b)

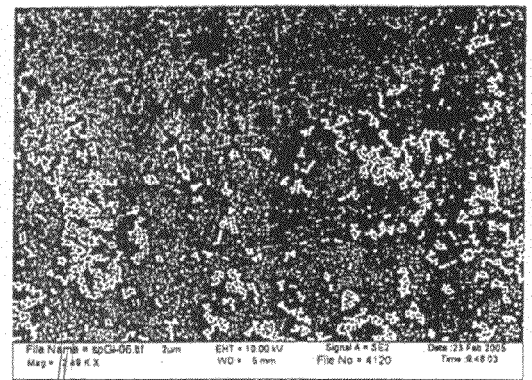
a)
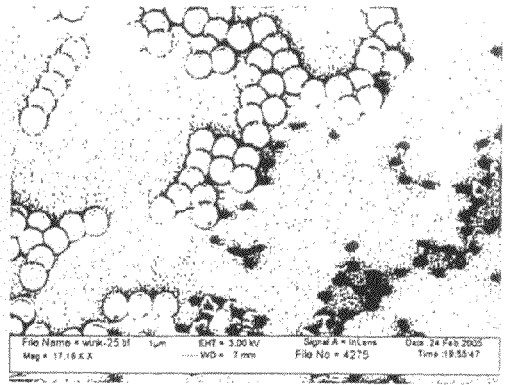
b)
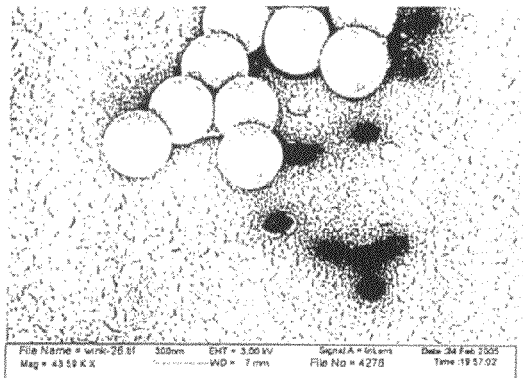
c)
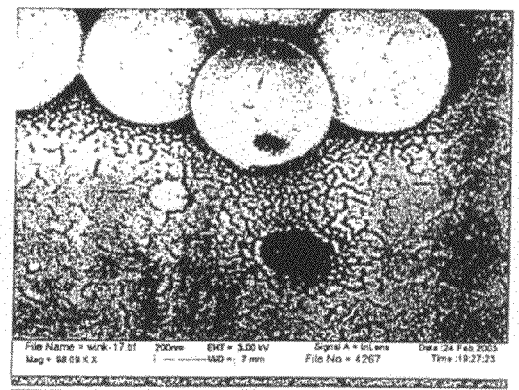
d)
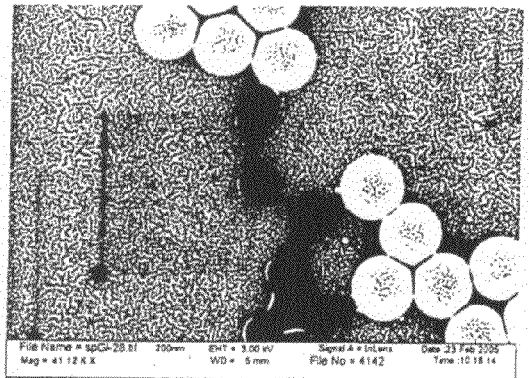
e)
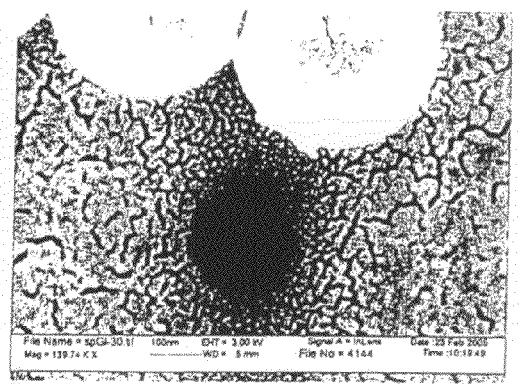
f)
Figures 6 a - f

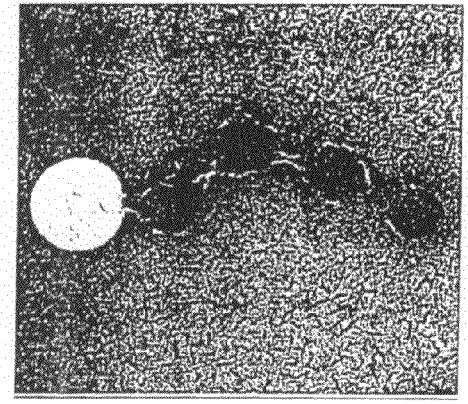
g)
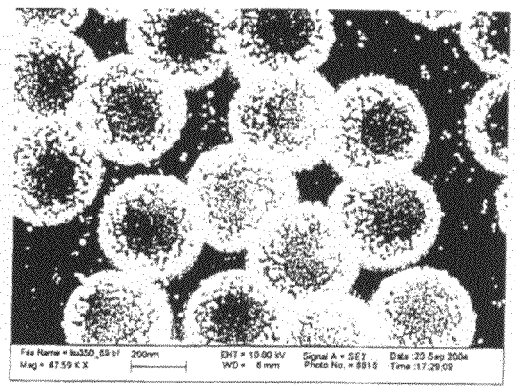
h)
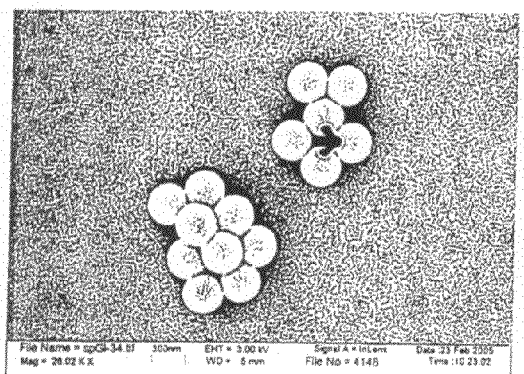
i)
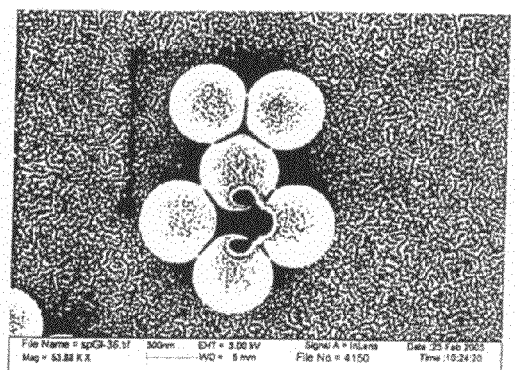
j)
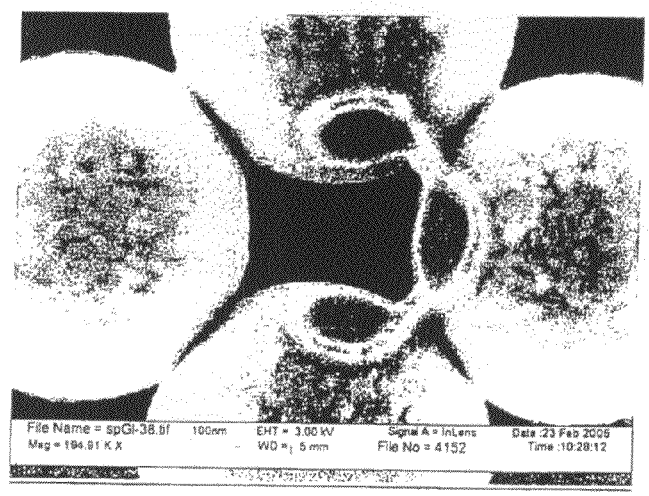
k)
Figures 6 g - k

SENSOR CHIP WITH CONNECTED NON-METALLIC PARTICLES COMPRISING A METALLIC COATING

CROSS REFERENCE TO RELATED APPLICATIONS

This application is a National Stage of International Application No. PCT/EP2006/003714 filed on Apr. 21, 2006, claiming priority based on European Patent Application No. 05008931.7, filed Apr. 22, 2005, the contents of all of which are incorporated herein by reference in their entirety.

TECHNICAL FIELD

The present invention relates to a chip comprising a layer of non-metallic particles with a metallic coating, a method for preparing said chip, an optical device comprising said chip and an analytical method using said chip.

BACKGROUND ART

Most of today's bioanalytical methods, such as immunoassays or hybridisation assays, require the use of labels, such as fluorescent labels, for the detection of the analyte. The use of such labels is, however, undesirable for a number of reasons: The necessity of washing the sample prior to the measurement is time-consuming and may also prevent the observation of transient interactions, low affinity binding events and binding kinetics. Moreover, the introduction of labels is costly and may alter the biological system under study in an undesirable and sometimes unpredictable manner. Finally, insufficient knowledge of the labeling efficiency may result in false results in biomedical analysis.

One technique allowing the label-free detection of an analyte involves surface plasmon resonance (SPR). The surface plasmon is a propagating wave of collectively oscillating free electrons at an interface between a thin metallic film and a dielectric material. As the propagation of the wave is influenced by the dielectric constant at the interface, adsorption processes at the interface can be sensitively detected. SPR sensors are commercially available, e.g. under the trade name BIAcore from Pharmacia Biosensor, Piscataway, N.J., USA.

A major limitation of these SPR sensors is the fact that the surface plasmon in e.g. gold layers propagates over comparably large distances, prohibiting their use for the detection of a plethora of different analytes that is needed in parallel, miniaturized biological assays such as protein arrays or DNA arrays.

Proposals have been made to use gold nanoparticles to exploit the phenomenon of localized or colloidal SPR. WO03/050291 describes a sensor obtained by depositing gold or silver nanoparticles on optically transparent substrates such as glass. US 2003/0174384 A1 describes the use of so-called gold nanoshells on top of a gold surface.

EP 0 965 835 A2 and Sensors and Actuators B 2000, 63, pp. 24-30 describe the formation of a monolayer of polystyrene particles on which a gold coating was subsequently formed by thermal evaporation, thereby forming cap-shaped gold nanoparticles. These sensor chips are reported to show a good sensitivity.

SUMMARY OF THE INVENTION

In light of this prior art, it is the object underlying the present invention to provide an optical device and a sensor chip showing an improved suitability for detecting analytes.

It is a further object of the present invention to provide an analytical method that allows the label-free and parallel detection of different analytes.

To achieve these objects, the present invention provides a chip comprising a substrate with at least one, optionally dielectric, surface and, on top of said at least one surface, a layer of particles having a non-metallic core and a coating made of a metal or a metal alloy, characterized in that each non-metallic core, on average, forms a metal-surrounded contact point, a so-called aperture, with at least one other non-metallic core and/or the substrate surface.

The invention also provides a method for preparing a chip, comprising the steps of
 adsorbing non-metallic particles on said surface of the substrate, and, subsequently,
 adsorbing colloids of a metal or a metal alloy on said non-metallic particles,
 or, alternatively, sputtering metal clusters or metal alloy clusters on said non-metallic particles,
 to provide the coating made of a metal or a metal alloy, and a chip which is obtainable by said method.

The inventors have surprisingly found that the chips of the present invention provide a significant increase in sensitivity in comparison to the surfaces comprising cap-shaped gold nanoparticles known from EP 0 965 835 A2, and in comparison to systems as described in US 2003/0174384 A1, where the particles comprise a closed shell.

The present invention also provides an optical device for the detection of an analyte, comprising the chip of the present invention, an optical system for irradiating said chip, and a detection system for detecting the light reflected, transmitted, scattered or diffracted from said chip surface.

Finally, the present invention provides a method for determining the concentration of an analyte, comprising the steps of
 detecting the light reflected, transmitted, scattered or diffracted from the chip according to the present invention,
 bringing a solution potentially containing one or more analytes in contact with said chip, and
 detecting the light reflected, transmitted, scattered or diffracted from said chip surface during or after exposure to the solution.

BRIEF DESCRIPTION OF THE DRAWINGS

FIGS. 5a-c give cross sections through the center of the contact point of two particles in contact. FIG. 5a shows the metallization of the particles by evaporation according to EP 0 965 835 A2 and Sensors and Actuators B 2000, 63, pp. 24-30 (cf. comparative example 1)); FIGS. 5b and c show metallization according to the present invention, e.g. by sputtering (cf. example 3) or the Layer-by-Layer deposition of colloidal metal particles (cf. example 2); FIG. 5d shows metallization of a particle not in contact with other particles. The metallic coating covers both, the particle and the substrate, thereby forming an aperture at the particle/substrate interface; FIG. 5a); FIGS. 5b and c)

FIGS. 6a-k show a method for verification of apertures between particles and/or the substrate by using SEM. FIGS. 6a and b show a chip surface, where part of the previously adsorbed particles has been removed by use of an adhesive tape; FIGS. 6c and d show contact points between particles still present on the surface and removed, formerly adjacent, particles. The former presence of the removed particles can be judged from the apertures in the metal coating of the substrate; FIGS. 6e and f show top views of similar areas as shown in FIGS. 6c and d. Metallic residues on the particles directing towards the former position of removed particles indicate that the metallic coating connects neighbouring particles; the connections can also be observed by inspection of the particle contacts; FIG. 6g shows residues on the substrate surface indicating that the formerly present particles were connected to the metal coating of the substrate; FIG. 6h shows particles stripped off the substrate by means of a double adhesive tape. The tape was then mounted on the SEM sample holder upside down for inspection of the particle surface formerly in contact with the substrate. Clearly, the formation of apertures with the substrate can be identified; FIGS. 6i-k show the formation of apertures between particles of the first and second particle layer. Only a single particle has been removed, formerly in contact with three adjacent particles below. The metallic rims surrounding the non-metallic contact points is clearly discernible.

DETAILED DESCRIPTION OF THE INVENTION

The Substrate

Figure 1:
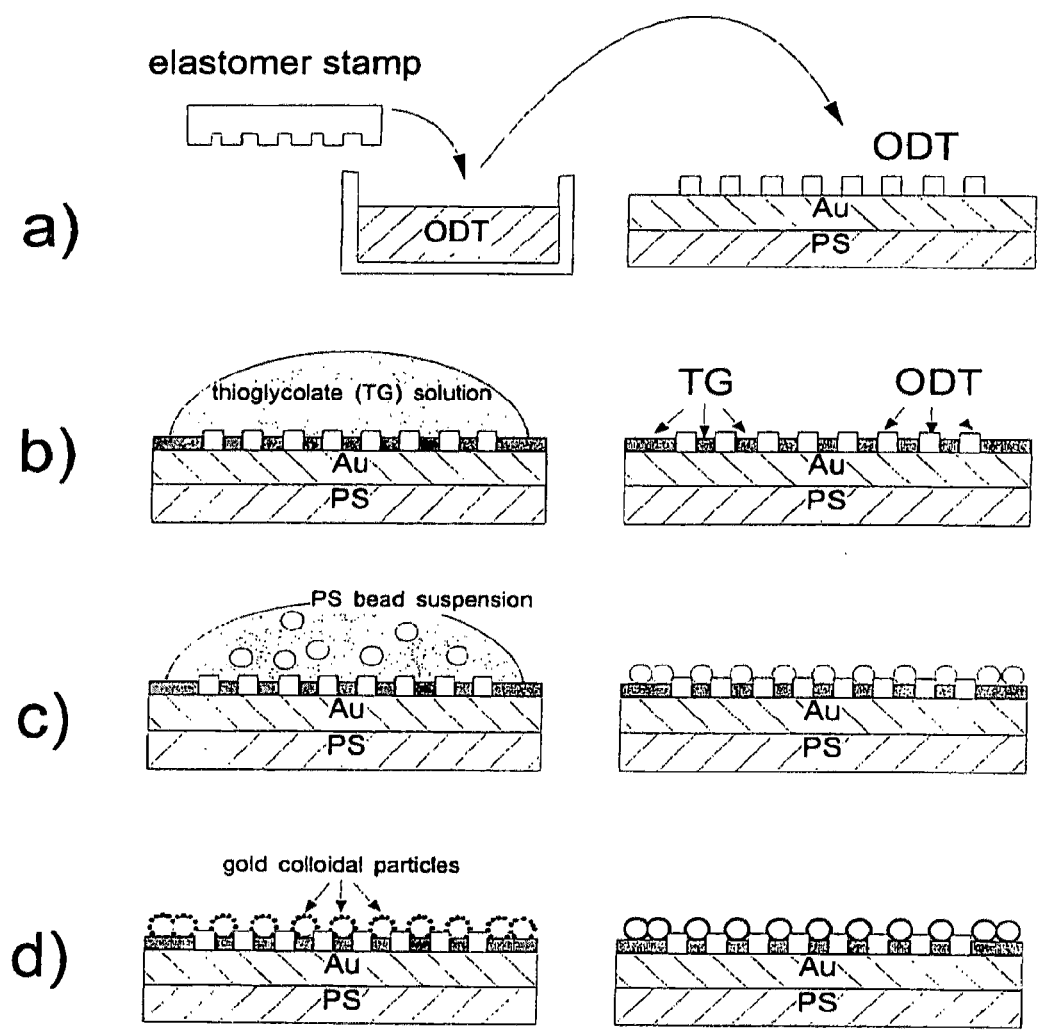
FIG. 1 illustrates a preferred method for preparing the chips of the present invention. (a) Surface functionalization of the gold-coated polystyrene (PS) substrate via microcontact printing of a hydrophobic thiol (octadecanethiol, ODT); (b) Filling of the gaps between printed ODT regions via thioglycolate (TG); (c) Adsorption of PS beads from aqueous solution via 1-ethyl 3-(3-(dimethylamino)propyl)carbodiimide hydrochloride (EDC) chemistry onto TG-coated regions; (d) decoration of the PS beads with colloidal gold particles and subsequent electroless plating to form a gold coating around the PS particles (for details, cf. examples 1 and 2).

The chip comprises a substrate with at least one surface. The shape of the substrate is not limited and may be flat or curved. For example, the substrate may have a circular cross-section. In a preferred embodiment, however, the substrate is flat. The substrate may be comprised of any suitable material known to those skilled in the art. Illustrative examples of suitable materials for use as the substrate include, but are not limited to, the following: glass; quartz; organic substrates, such as polycarbonates, polyolefins (e.g. polystyrene) and acrylic and methacrylic resins (e.g. polymethyl methacrylate, PMMA); inorganic materials, such as germanium, gallium arsenide, silicon, silicon-derived materials (e.g. fused silica, silicone gels and polysiloxanes) and tin derived materials (e.g. tin oxide and indium-doped tin oxide) and the like. Particularly preferred materials are glass, silicon and organic substrates such as polystyrene or PMMA substrates.

In another preferred embodiment, the substrate consists of a waveguiding material or comprises waveguiding elements which allow the transduction of light signals through the substrate. For example, a waveguiding material consists of a polymer substrate with refractive index n1, in which another material, e.g. a second polymer, with refractive index n2>n1 is integrated in such a way, that the light can be guided within the second material by total internal reflection. Alternatively, the second material with n2>n1 can be generated from the integrating material by physico-chemical modification of the latter, e.g. by UV treatment of the latter in selected regions. According to the present invention, the non-metallic cores preferably contact the surface of the material with the higher refractive index. The shape of the waveguiding material is not limited and may be flat or curved. In a preferred embodiment it is a flat substrate or a fibre.

The surface of the substrate may be composed of the same material as the bulk substrate material or it may be composed of a separate metallic or non-metallic layer coated on the substrate. This metallic or non-metallic layer can consist of single or multiple materials and/or sublayers. Each of the sublayers may be homogeneous or patterned. Patterned sublayers composed of metallic and non-metallic areas may provide resonant enhancement of optical signals and/or transport of electrical signals. Patterned sublayers may also be used for the directed adsorption of non-metallic particles onto selected areas of the substrate. The layer of the single or multiple materials and/or sublayers may be the waveguiding material described above. Further, the layer of the single or multiple materials and/or sublayers may contain fluorescent dyes and/or other optically active materials.

In a preferred embodiment, the layer coated on the substrate is composed of a metal or a metal alloy, preferably a transition metal or a transition metal alloy. Metals that are particularly well suited for use in such layers include, but are not limited to aluminium, gold, silver, copper, platinum, palladium, lead, iron or the like. Gold, silver, palladium and/or platinum are preferred. Alloys or non-homogeneous mixtures of such metals may also be used. The thickness of the layer composed of a metal or a metal alloy (preferably a transition metal or transition metal alloy) is preferably between 2 and 500 nm, more preferably between 5 and 100 nm, and most preferably between 10 and 50 nm.

The metal layer in turn may be coated with a non-metallic, preferably dielectric layer. The non-metallic layer has preferably a thickness of less than 100 nm, more preferably 1 to 50 nm, and may, e.g., consist of polyelectrolytes, spin-coated polymers, spin-on glass, SiO$_2$, semiconductors such as silicon, germanium, or gallium arsenide, or indium-doped tin oxide. In a preferred embodiment, the dielectric layer is composed of a monolayer of organic molecules, e.g. of an alkanethiol or a silane which may or may not be modified and which may or may not form a SAM.

In a preferred embodiment, the uppermost sublayer may be patterned with regions having distinct physico-chemical properties, such as regions with different hydrophilicities or chemical functional groups.

In a preferred embodiment, the pattern provides chemical structures (e.g. squares) of 400 nm$^2$ to 10000 μm$^2$, more preferably 1 μm$^2$ to 1000 μm$^2$, that are separated by gaps of 20 nm to 100 μm, more preferably 1 μm to 30 μm. In another preferred embodiment, the pattern consists of circles embedded in a matrix material of different chemical functionality. The preferred diameter of the circles ranges from 100 nm to 100 μm, more preferably from 1 μm to 30 μm.

For example, the patterning can be provided by microcontact printing, photolithography, or electron beam lithography.

Chemically-patterned gold surfaces (e.g. 10 to 50 nm gold layers directly evaporated onto an organic substrate such as polystyrene) can be prepared using microcontact printing providing distinct chemical contrast between different surface areas (Kumar et al., Science 1994, 263, pp. 60-62). For example, a microstructured elastomer stamp is inked with a solution of a first thiol (e.g. a 1 millimolar (mM) ethanolic solution of 1 octadecanethiol) providing a comparatively hydrophobic surface. After drying, the stamp is softly pressed onto the substrate (e.g. for 10 seconds to 1 minute). After removal of the stamp, the intermediate space is filled by immersing the substrate into a solution of a hydrophilically functionalized thiol (such as 16-mercaptohexane decanoic acid). Thus, a surface with patterns of COOH- and CH$_3$-terminated thiolates is obtained. The geometry and size of the patterns depend on the microstructure of the elastomer stamp. Preferred lateral dimensions range from 0.5 to 50 μm. A suitable patterning process is described in Kaltenpoth et al., Adv. Materials 2003, 15, No. 13, pp. 1113 to 1118.

Alternatively, the patterning of the surface properties may be achieved by photochemical reactions. Upon irradiation through a mask, molecules with photolabile groups such as benzophenone, diazirin or azide moieties are bound to organic matrices in well-defined structures. Non-derivatized surface areas can be reacted with other types of molecules in successive steps. Problems in surface derivatization occur as a result of unwanted parallel chemical reactions and possible fragmentation processes during illumination. This dilemma can be overcome by temporarily masking the chemical functionalities with non-photolabile protective groups, which are quantitatively removed after the immobilization process. The dimensions of the generated chemical structures range from 500 nm to 1 mm (Ph.D. Thesis, Jürgen Pipper, Universität Heidelberg, 1999).

Chemical patterning on the nanometer scale may be achieved by electron beam lithography. For example, amino-terminated silane SAMs deposited on Si substrates can be patterned with a resolution of about 80 nm by electron-induced cleavage of the amino group. The chemical surface structures can act as templates for the directed adsorption of non-metallic particles on the areas not exposed to the beam (Harnett et al., Appl. Phys. Lett. 2000, 76, No. 17, 2466-2468). Alternatively, the terminal NO$_2$ groups of 4'-nitro-1,1'-biphenyl-4-thiolate SAMs on gold can be converted to NH$_2$ groups by electron beam irradiation, while the underlying aromatic film is cross-linked ("chemical nanolithography"; Gölzhäuser et al., Adv. Mater. 2001, 13, No. 11, pp. 806-809). The smallest structures presently achievable are lines of 20 nm width. The generated, NH$_2$-terminated nanostructure may serve as a template in subsequent coupling reactions, thus, forming the basis for a variety of chemical surface modifications.

The Non-Metallic Cores of the Particles

Suitable non-metallic core materials include, but are not limited to, inorganic materials such as silicon dioxide, gold sulphide, titanium dioxide, germanium, gallium arsenide, silicon, silicon-derived materials (e.g. fused silica, silicone gels and polysiloxanes) and tin-derived materials, polymethyl methacrylate (PMMA), polystyrene, other macromolecules such as dendrimers, polyelectrolytes, hydrogels, micelles and vesicles. The particles may contain fluorescent dyes, optically active materials (i.e. materials which absorb light in a first wavelength range and which then emit light in a second wavelength range that is different from the first wavelength range) and/or be functionalized with chemical groups that are suitable for crosslinking the particles such as amine groups or carboxylate groups. Preferred non-metallic materials are dielectric materials. A preferred dielectric core material is silicon dioxide or polystyrene (preferably containing sulfate groups). The mean average diameter of the non-metallic cores of the particles is preferably in the range of 10 to 1000 nm, more preferably 50 to 700 nm, and most preferably 80 to 500 nm. For some applications, a mean average diameter of 10 to 150 nm is particularly advantageous. In case of a substrate comprising a waveguiding material, the average diameter is preferably in the range of 3 to 30 μm. The shape of the particles may be spherical or non-spherical such as needle shape, cube shape, pyramids etc. Preferred are spherical cores. In a preferred embodiment, mono-disperse non-metallic core materials are used having a standard deviation of the average diameter of the core of 15% or less, more preferably 10% or less, most preferably 5% or less. The mean average diameter of the particles is determined by laser light scattering measurements (Rayleigh scattering).

Adsorption of the Non-Metallic Cores on the Substrate

In contrast to the chips described e.g. in US 2003/0174384 A1, where gold nanoshells are adsorbed on top of a gold surface, the chip of the present invention is produced by first adsorbing the non-metallic core particles on the substrate. To achieve this, the non-metallic core particles are suspended in a suitable solution and then adsorbed on the substrate surface.

To mediate adsorption of the particles on the substrate, any of the commonly known methods can be utilized (Himmelhaus and Takei, Phys. Chem. Chem. Phys. 2002, 4, pp. 496-506). For example, physical procedures based on surface tension (Lenzmann et al., Chem. Mater. 1994, 6, pp. 156; Deckman et al., J. Vac. Sci. Technol. B 1989, 7, pp. 1832) and capillary forces (Rakers et al., Langmuir 1997, 13, pp. 7121; Denkov et al., Langmuir 1992, 8, pp. 3183) can be applied. Additional control can be gained by using hydrodynamic flow fields in confined geometry or cooling the suspension to minimize Brownian motion (Burmeister et al., Chem. Eng. Technol. 1998, 21, pp. 761). Further, by means of macromolecules added to the suspension, entropic forces can be generated, which induce attractive forces between the non-metallic particles and the substrate (Rudhardt et al., Phys. Rev. Lett. 1998, 81, pp. 1330). Besides physical means, also chemical methods can be applied to control surface adsorption of the particles. For example, by addition of salts or chemicals that alter the surface properties, such as surfactants, to the suspension, the surface charge of the non-metallic particles can be changed, thus altering the interaction between the particles as well as between particles and substrate (Chen et al., Langmuir 2000, 16, pp. 7825; Himmelhaus and Takei, Phys. Chem.

Chem. Phys. 2002, 4, pp. 496). In general, any method which alters the stabilization of the colloidal suspension, i.e., reduces the effective repulsion among the particles as well as between particles and surface, can be utilized for the formation of an adsorbate layer of non-metallic particles on the surface.

In a preferred preparation scheme, mono-disperse, preferably sulphated polystyrene spheres with an average diameter of 10 to 800 nm are used with further processing as follows: The sphere suspension (preferably containing 1 to 4 vol. % spheres) is mixed with deionized water and a phosphate buffer at a pH of 7.6, preferably in a volume ratio of (1 to 3):(1 to 3):(1 to 3). Before mixing, EDC is added to the phosphate buffer. Then, the activated suspension is placed onto a substrate within 5 minutes. In the case of adsorption of particles on native gold a value of 1 to 10 mg EDC per ml buffer solution yields the best results, with respect to the uniformity of particle adsorption on the surface. The suspensions are allowed to sit on the surface (e.g. for one hour), and then are rinsed off with a copious amount of deionized water. Finally, thus obtained layer of polystyrene particles is dried in air.

The non-metallic cores can be adsorbed as a monolayer or as multiple layers. The formation of monolayers is particularly preferred. Depending on the method applied for the formation of the monolayer, the particles can achieve regular or random packing. Random packing is preferred because of lack of diffraction-related problems and ease of production of larger areas. With the coating process of the present invention, very high random packing densities of more than 35%, preferably more than 45%, and most preferably more than 50% can be achieved. Note that the maximum packing density for random close-packing is 54.7% of total coverage which is the jamming limit of the random sequential adsorption model for spheres (Hinrichsen et al., J. Stat. Phys. 1986, 44, pp. 793).

It may also be preferred to use particles of at least two different mean average diameters. In a particularly preferred embodiment, a non-metallic core with a mean average diameter in the range of 200 to 800 nm is used in combination with a non-metallic core with a mean average diameter in the range of 10 to 100 nm. On the surface, the smaller particles may fill the gaps between the larger particles and thus increase the overall particle density on the surface.

Figure 3:
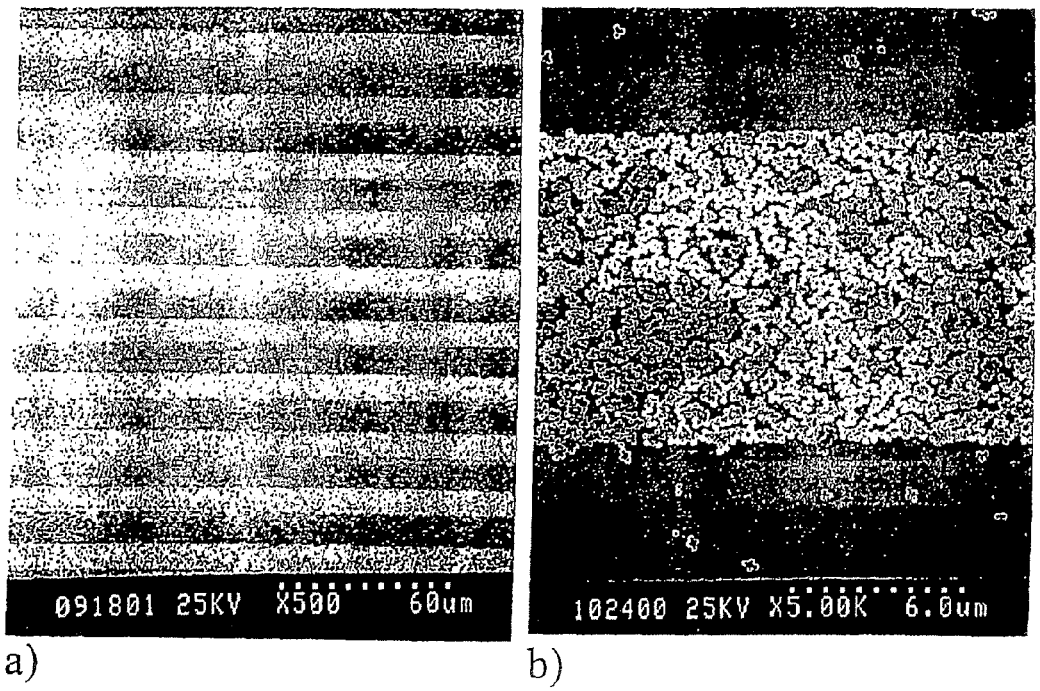
FIG. 3 shows SEM micrographs of patterned chip surfaces prepared according to example 1 prior to metallization.

If the substrate is provided with a patterned layer that provides regions of different physical or chemical properties such as tailored topologies, different hydrophilicities or chemical functional groups, the adsorption of the non-metallic core particles may be carried out in such a manner that the particles adsorb on only one of these regions, e.g., in case of charged surfaces, the region with a charge opposing that of the particles (Chen et al., Langmuir 2000, 16, pp. 7825), in case of hydrophilic/hydrophobic patterns, the more hydrophilic regions (Aizenberg et al., Phys. Rev. Lett. 2000, 84, pp. 2997), and in case of alternating regions of carboxylic and methyl functionalities, on the chemically active carboxylic groups. In the latter case, the adsorption can be mediated by addition of EDC (Himmelhaus and Takei, Phys. Chem. Chem. Phys. 2002, 4, pp. 496-506), which is a preferred method according to the present invention. FIG. 3 shows a patterned particle monolayer, which was fabricated by microcontact printing of a chemical pattern on a gold surface and addition of EDC to the particle suspension prior to exposure to the chemical pattern (for details, cf. FIG. 1 and example 1).

In case of a substrate comprising waveguiding elements, the patterned layer can be used to provide optical coupling between the non-metallic particles and the waveguiding elements.

Metallization of the Non-Metallic Cores

According to a preferred embodiment of the present invention, colloids of a metal or metal alloy, preferably a transition metal or a transition metal alloy, are adsorbed on the surface comprising the non-metallic particles and/or the substrate.

The colloids may have a spherical or non-spherical shape, such as needle-like or triangular. The colloids can be adsorbed in a pattern if embedded in an organic shell (Spatz et al., Macromol. 1996, 29, pp. 3220).

The adsorption method depends on the nature of the non-metallic core. For example, for silicon dioxide particles, the surface may be activated with (aminopropyl)trimethoxysilane, on which the colloids are subsequently adsorbed, similar to the process described by Halas and coworkers in Langmuir 1998, 14, pp. 5396, for particles in solution. For polystyrene particles, the method described by Lirtsman et al. in Adv. Mater. 2001, 13, pp. 1253, for particle suspensions can be adapted, as described in more detail in the examples.

Subsequent to the adsorption of the colloids, the material may be subjected to an electroless plating step (e.g. using transition metal salts and a reducing agent) to increase the (transition) metal or (transition) metal alloy coverage and/or to improve the electrical contacts between the colloids. The procedure of colloid deposition and/or electroless plating may be repeated one or several times to achieve a highly conductive coating as described in Kaltenpoth et al. (Adv. Mater. 2003, 15, pp. 1113).

Alternatively, the coating can be obtained by sputtering with metal or metal alloy, preferably transition metal or transition metal alloy, as known to those skilled in the art.

In a preferred embodiment, the coating of the non-metallic cores consists of different metallic sublayers, separated from each other by non-metallic interlayers, which may contain fluorescent dyes or other optically active materials. Such non-metallic interlayers can for example be prepared by evaporation or sputtering of a non-metallic material. Alternatively, the layer-by-layer technique can be used, in particular to incorporate dyes or other optically active materials into the interlayers (Campbell et al., Chem. Mater. 2005, 17, pp. 186-190; Decher and Schlenoff (eds.), Multilayer Thin Films, Wiley-VCH 2003).

According to a preferred embodiment of the present invention, the coating of the non-metallic cores essentially covers the free surface of the non-metallic cores in a uniform manner. That is, the coating is formed on the entire surface that is available for adsorption, this surface being the particle surface with the exception of the areas that are not accessible due to their contact to another particle or to the substrate surface. The coating may consist of isolated colloids, a contiguous colloid layer, or a continuous layer of a (transition) metal or a (transition) metal alloy. The contiguousness of the coating may be tailored, e.g., by successive colloid deposition and electroless plating steps a described above.

Characterization of the Chip Surface

In contrast to the method described by Himmelhaus and Takei (Phys. Chem. Chem. Phys., 2002, 4, 496-506; Sensors and Actuators B 63 (2000) 24-30), where gold was thermally evaporated on a surface coated with polystyrene particles, thereby providing a surface with cap-shaped gold nanoparticles, the chip of the present invention comprises metal-coated particles with non-metallic cores wherein each non-metallic core, on average, forms a metal-surrounded contact point, a so-called aperture, with at least one other non-metallic core and/or the substrate surface.

Figure 5:
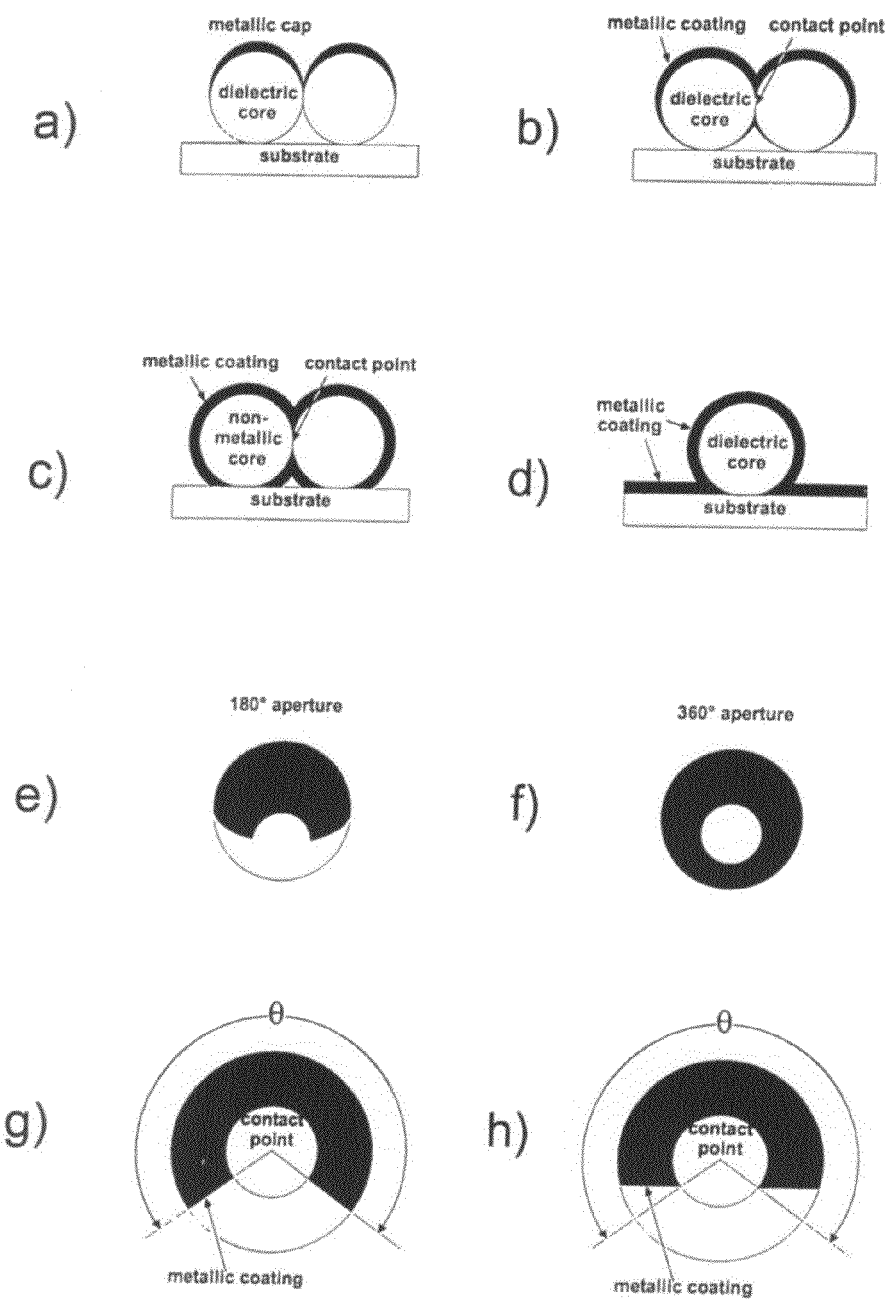
FIGS. 5a-d visualize the formation of non-metallic contact points between neighboring particles and/or the surface, which are surrounded by the metallic coating.
FIG. 5e shows a contact point, which is surrounded by a metallic coating to an extent of θ=180°, as achieved by metallization via evaporation (cf.
FIG. 5f shows a contact point, which is surrounded by a metallic coating to an extent of θ=360°, as can be achieved by metallization according to the present invention (cf.
FIGS. 5g and h show examples of contact points of the non-metallic particles, which are surrounded by the metallic coating to an extent of θ>220°.
Figure 8:
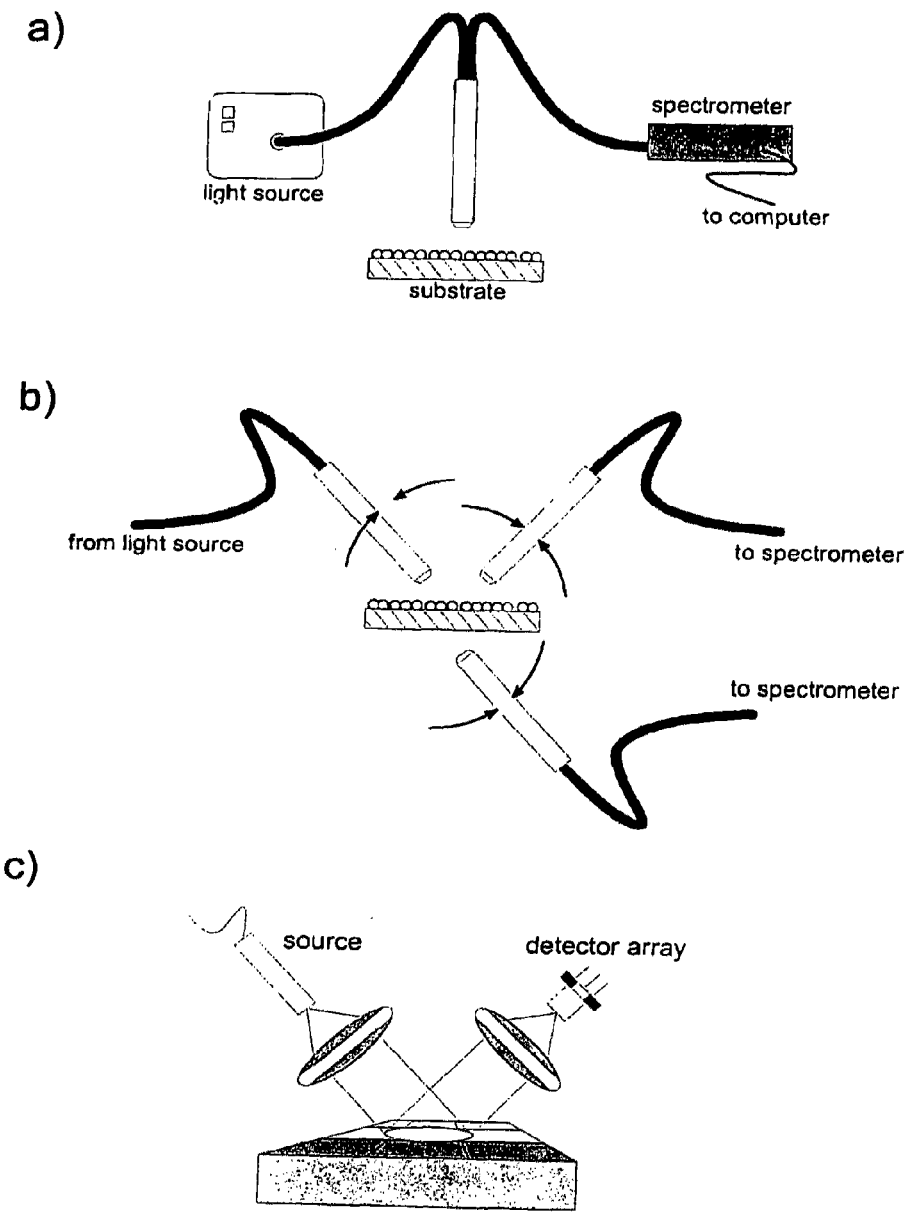
FIGS. 8a and b illustrate the optical set-up for acquisition of the extinction spectra using a fibre-optical probe to detect the light reflected, scattered, and/or diffracted from or, transmitted through the surface. For detection of scattering, an integrating sphere can be additionally used.
FIG. 8c gives an example for an alternative imaging set-up for measurements. Alternatively, simultaneous laterally resolved measurements can also be performed in transmission through the substrate.

The contact points between the cores of the particles are preferably characterized such that on average they are surrounded by the metal or metal alloy coating to an extent of $\theta > 220$ degrees (c.f. FIGS. 5$g$ and $h$). In a preferred embodiment, the metal or metal alloy coating contiguously connects particles with a common contact point (FIGS. 8b and c).

In the case of spherical particles, the coating is also present in the hemisphere of the particles directed towards the substrate surface.

In the case of a particle monolayer, each non-metallic core, on average, preferably contacts both at least one other, preferably at least 1.5 other non-metallic core(s) and the substrate surface. In the case of particle multilayers, each non-metallic core, on average, preferably contacts at least 2 other non-metallic cores.

In case that on average less than one contact point between the cores of the particles is formed, the metal or metal alloy covers the cores of the particles and the substrate in a contiguous way (FIG. 5d).

The metallic coating preferably uniformly covers the free surface of the non-metallic cores, i.e., the surface that is not in contact with another core or with the substrate surface.

Scanning Electron Microscopy (SEM) can be used to prove the existence of contact points, and to characterize the surrounding metal or metal alloy coating (e.g. transition metal or transition metal alloy coating) as well as the formation of a contiguous connection between particles and/or the substrate. For this, part of the particle layer can be pulled off the substrate by means of a double adhesive tape (FIG. 6) and the border between still and formerly adsorbed particles is analyzed. Examples of an SEM analysis following this procedure are given in FIGS. 6a-k.

In case of non-spherical particles, the same analytical procedure for the verification of contact points may be applied as described above for spherical particles. However, the shape of the apertures, i.e., the holes in the metal coating, will then depend on the symmetry of the contact area.

The Optical Device for the Detection of an Analyte

The chips of the present invention show unique optical properties that make them particularly useful for use in sensors and biochemical arrays. It has been demonstrated that layered structures composed of thin metal films, dielectric materials, and gold nanoparticles exhibit distinct optical extinction characteristics in the IR to UV regime. The invention thus also provides an optical device for the detection of an analyte comprising the chip of the present invention, an optical system for irradiating said chip, and a detection system for detecting the light reflected, transmitted, scattered, or diffracted, preferably reflected, from said chip surface. It was also noticed that the measured optical extinction spectrum is sensitively affected by adsorption of organic molecules onto the chip surface. As surprisingly found by the present inventors, the chip according to the present invention is significantly more sensitive than the prior art chips.

The irradiation or excitation light excites collective oscillations of the conduction electrons (plasmon resonance) within the metallic coating of the non-metallic cores and/or the substrate. The excitation of these collective oscillations causes a loss in the light reflected, scattered or diffracted from or transmitted through the surface, which can be spectrally analyzed, e.g. by means of a fibre optical spectrometer, to determine the characteristics of the surface plasmon excitation (e.g. resonance wavelength and peak absorbance). The resonance wavelength is typically located in the ultraviolet, visible, or infrared region of the spectrum. Laterally resolved information can be obtained, for example, by optical imaging of the light reflected, scattered or diffracted from or transmitted through the surface onto the active surface of a CCD detector. Alternatively, the reflected, transmitted, scattered, or diffracted light can be separated from the irradiation light (excitation light) by using dark field microscopy, reflection microscopy, total internal reflection microscopy or scanning near field optical microscopy. The spectral signature of the reflected, transmitted, scattered or diffracted light may then be analyzed and recorded by a CCD camera, one or more photodiodes, photo multipliers and/or photodiode arrays in combination with a spectrometer, a monochromator and/or a dichroic mirror.

A simple optical device that can be used with the chips consists of a white light source connected to an optical fibre for illumination of the sample, a second fibre for detecting the light reflected, scattered or diffracted from or transmitted through the chip, and a fibre-optical spectrometer connected to an electronic device for data storage and evaluation (FIGS. 8a and b). If laterally resolved information is desired, the detection fibre and chip can be scanned laterally with respect to each other. Alternatively, the optical fibre used for detection can be replaced by an optical system, which optically images the entire chip surface onto the active area of a CCD chip or a diode array or a related laterally resolved optical detection device (FIG. 8c). The white light source can be replaced by one or more monochromatic sources, e.g. 3 to 5 LEDs or laser diodes operating at different wavelengths, or can be connected to a spectral filtering system prior to illumination of the chip surface to facilitate the acquisition of spectrally and laterally resolved information.

If a small number of monochromatic or narrow band light sources, such as LEDs or laser diodes, is utilized, the changes of the reflected, transmitted, scattered or diffracted light intensities at the respective wavelengths due to changes in optical properties in close vicinity of the surface can be used to determine the changes of the entire spectra, for example by interpolation or by fitting the spectra to model functions.

In an alternative approach, whispering gallery modes inside the surface-adsorbed dielectric particles are excited, for example by optical coupling between the non-metallic particles and a waveguiding material or waveguiding elements, such as a planar waveguide or an optical fibre. In this case the use of non-metallic particles with a diameter>5 µm is advantageous for light excitation in the visible and/or NIR region of the electromagnetic spectrum (Oraevsky, Quantum Electronics 2002, 32, pp. 377). Also, in this case the particles are preferably deposited on the waveguiding surface in such a way, that they have a controlled number of contact points with neighbouring particles, for example no contact at all. This can be achieved, for example, via application of microcontact printing (cf. example 1) by printing square patterns with a size smaller than the particle diameter. Another example of controlling contact points between particles is the arrangement of a controlled number of particles in lines. Again, this can be achieved via microcontact printing (Kaltenpoth et al., Adv. Mater. 2003, 13, pp. 1113).

Immobilization of Binding Agents

To render the chip selective for specific analytes, it is preferred to coat the chip surface with binding agents that are capable of (preferably reversibly) binding an analyte, such as proteins, peptides, and nucleic acids. Methods for conjugating binding agents to metal surfaces are known and are equally suitable for derivatizing the chip surface of the present invention. For example, the chip of the present invention can be chemically modified by using transition metal (e.g. gold)-thiol chemistries. For example, the surface with the metal-coated non-metallic cores can be immersed in a solution of thiol molecules having an amino group such as aminoethanethiol so as to modify the chip surface with an amino group. Next, biotin modified with N-hydroxysuccinimide suspended in a buffer solution of pH 7-9 can be activated by EDC, and added to the chip surface previously modified by an amino group. As a result, an amide bond is formed so as to modify the metal-coated non-metallic cores with biotin. Next, avidin or streptavidin comprising four binding sites can be bound to the biotin. Next, any biotin-derivatized biological molecule such as protein, peptide, DNA or any other ligand can be bound to the surface of the avidin-modified metal-coated non-metallic cores.

Alternatively, amino-terminated surfaces may be reacted with an aqueous glutardialdehyde solution. After rinsing the substrate with water, it is exposed to an aqueous solution of proteins or peptides, facilitating covalent coupling of the biomolecules via their amino groups (R. Dahint et al., Anal. Chem., 1994, 66, 2888-2892). If the chip is first carboxy-terminated, e.g. by exposure to an ethanolic solution of mercapto undecanoic acid, the terminal functional groups can be activated with an aqueous solution of EDC and N-hydroxysuccinimide). Finally, proteins or peptides are covalently linked to the activated surface via their amino groups from aqueous solution (Herrwerth et al., Langmuir 2003, 19, 1880-1887).

A general problem in controlling and identifying biospecific interactions at surfaces is non-specific adsorption. Common techniques to overcome this obstacle are based on exposing the functionalized substrates to other, strongly adhering biomolecules in order to block non-specific adsorption sites. However, the efficiency of this approach depends on the biological system under study and exchange processes may occur between dissolved and surface bound species. Moreover, the removal of non-specifically adsorbed biomolecules may require copious washing steps, thus, preventing the identification of specific binding events with low affinity.

A solution to this problem is the integration of the binding agents into inert materials, such as films of poly- (PEG) and oligo(ethylene glycol) (OEG). The most common technique to integrate biospecific recognition elements into OEG-terminated SAMs is based on co-adsorption from binary solutions, composed of protein resistant EG molecules and a second, functionalized molecular species suitable for binding agent coupling (or containing the binding agent itself). Alternatively, also direct coupling of binding agent to surface-grafted end-functionalized PEG molecules has been reported.

Recently, a COOH-functionalized poly(ethylene glycol) alkanethiol has been synthesized, which forms densely-packed SAMs on gold surfaces. After covalent coupling of biospecific receptors, the films effectively suppress non-specific interactions while exhibiting high specific recognition (Herrwerth et al., Langmuir 2003, 19, pp. 1880-1887).

The binding entities immobilized at the surface may be proteins such as antibodies, peptides, oligonucleotides or DNA (which hybridize to a specific target oligonucleotide or DNA, e.g. a specific sequence range of a gene, which may contain a single nucleotide polymorphism (SNP), or carbohydrates). To reduce non-specific interactions, the binding entities will preferably be integrated in inert matrix materials.

The invention thus also provides a method for determining the concentration of an analyte, comprising the steps of bringing a solution potentially containing one or more analytes in contact with a chip of the present invention while irradiating the chip surface, and detecting the light reflected, scattered or diffracted from or transmitted through said chip surface. Alternatively, the reflected, transmitted, scattered or diffracted light may also be detected after removal of the solution. By comparing the optical surface properties prior to and after adsorption of the analyte, both qualitative and quantitative measurements become possible. More preferably, the signal intensity is recorded continuously. This allows further insights into the adsorption kinetics and enhances the usefulness of the claimed device.

The Microarray

In a preferred embodiment, a plurality of binding agents is immobilized on the surface in such a manner that different locations on the chip surface can be assigned to different binding agents. In other words, the invention also provides microarrays of binding agents such as nucleic acid arrays or peptide arrays. A microarray is a spatially defined ordered, miniaturized arrangement of a multitude of immobilized reagents. For example, the binding agents may be assigned to different locations by using spotting devices such as arrayers or microarray printers (see Angew. Chem. Int. Ed. 2002, 41, pp. 1276-1289).

Rather than immobilizing the complete binding agent molecules, the binding agent such as the peptides or nucleic acids may also be formed on the surface in situ. Combinatorial peptide synthesis may be performed with a modified color laser printer (A. Poustka et al., WO Patent 00/35940, 2000) allowing the transfer of "monomer toner particles" onto a support. The particles consist of protected amino acids or nucleotides and a "solid solvent". After forming a two-dimensional pattern of toner particles containing different amino acids on the surface, the temperature is raised above the particles melting point. Then, the solid solvent liquefies and the hitherto trapped monomers couple to the support. By repeating these steps in a combinatorial manner, many different binding agents may be generated on the surface. Alternatively, the technology described in EP-A-619 321 may also be used. If combinatorial synthesis is performed on a structured or non-structured layer of particles, label-free high-throughput screening of binding events is facilitated by locally testing for changes in the optical properties of the chip.

As a chip for the immobilization of a binding agent array, it is particularly preferred to employ chips wherein the particles are present in a pattern, as described above. It is particularly preferred to apply the binding agent selectively on the particle coated areas. For example, when the surface comprises square patterns of particle-coated areas, it is preferred to spot the binding agent onto these areas. This can be achieved by using binding agent volumes or binding agent particles (e.g. toner particles) that cover about the size of these areas or a slightly smaller area. This approach reduces cross-talk between the individual areas.

Other Applications

The chip and optical device using said chip described in the present invention basically measures changes in the dielectric properties in the immediate vicinity of the chip surface. Therefore, the invention can be applied to any application which can utilize changes in the dielectric properties, i.e. the refractive index, in vicinity of the chip surface as a measure, i.e. transducer mechanism, for the conversion of a physical or (bio-)chemical signal into an optical and/or electrical signal. For example, the chip and device can be used to trace temperature changes in a fluid in contact with the chip surface. In the same way, the concentration of solutes in mixed solutions, the inhomogeneity in flow profiles, for example due to turbulence, the concentration upon mixing of two different fluids, the changes in the density of viscoelastic or elastic materials in contact with the chip surface can be measured. Projections of turbulences in liquids could be monitored on the chip surface by use of laterally resolved detection mechanisms as described for the read-out of microarrays.

If the chip surface is coated with a material that is capable of changing its density and thus in its refractive index due to physical or chemical effects (e.g. forces or chemical reactions), the chip and the optical device can be used to monitor these changes. For example, a hydrogel can be immobilized on the chip surface, thus allowing to trace changes in the pH or salt concentration, the humidity of a gas, etc.

EXAMPLES

Example 1

Preparation of the Chip Surface Via EDC-Mediated Adsorption

Figure 2:
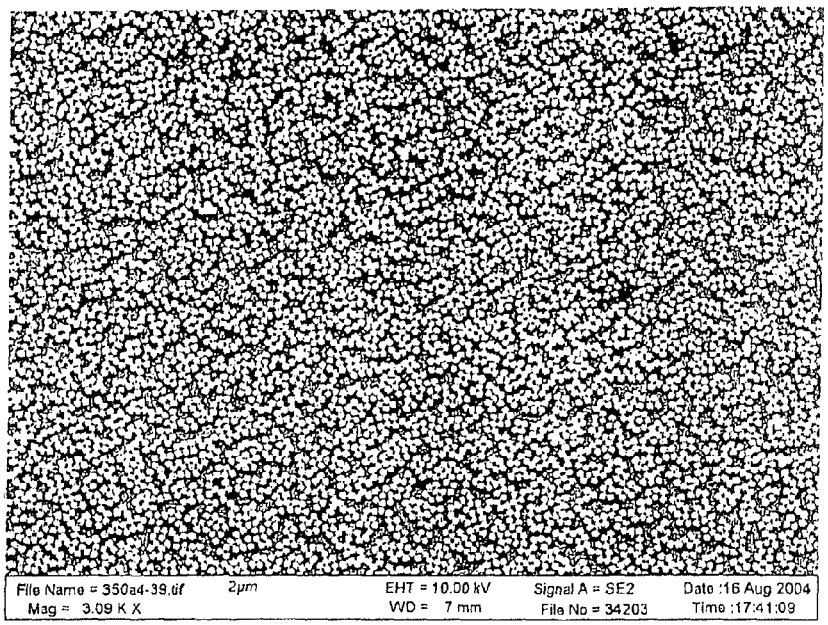
FIG. 2 shows a SEM micrograph of a chip surface prepared according the routine given in example 1 prior to metallization.

To obtain a chip surface coated with a densely packed layer of polystyrene (PS) nanobeads, we proceeded as follows: The inner side of the top of a polystyrene cell culture plate (FALCON, cat. #3002 from BD Co.), which is divided into 96 wells of ~9 mm diameter and a rim height of ~1 mm, was coated with a 20 nm thick film of gold (99.99%) by evaporation. The evaporator was equipped with a tungsten filament and operated at a base pressure of $5 \cdot 10^{-7}$ mbar. After evaporation, the gold film deposited within the wells of the substrate was exposed to an aqueous solution of a carboxyl-terminated alkanethiol (TG, 97%; 10 mM solution in deionized water) for 60 min to render the surface hydrophilic. After 60 min, the solution was rinsed off with deionized water. Then, the surface was exposed to an aqueous suspension of monodisperse polystyrene beads with an average diameter of 350 nm, prepared in the following way: 350 nm PS beads (standard deviation<5%; Polysciences, Warrington, Pa., USA) suspended in water were mixed with deionized water and phosphate buffer (pH 7.6) at a volume ratio of 2:1:3. Before mixing the suspension, a small amount of EDC {99%; Sigma-Aldrich} was added to the phosphate buffer to yield a ~3 mM EDC buffer solution, which then was used to prepare the suspension. The suspension was filled into the circular wells of the substrate and rested for one hour. Subsequently, it was rinsed off with a copious amount of deionized water and dried in air. Following this procedure, particle layers as displayed in FIG. 2 were obtained.

To obtain patterned PS bead layers, the procedure described above was modified in the following way (FIG. 1): Prior to exposure of the gold surface to the aqueous TG solution, a pattern of octadecanethiol (ODT) was formed on the gold surface via microcontact printing (Kumar et al. Science 1994, 263, pp. 60-62). Thereby, an elastomer relief stamp {poly(dimethylsiloxane)} was inked with an 1 mM ethanolic solution of ODT. After evaporation of the solvent, the stamp was softly pressed onto the gold surface, thereby transferring the ODT onto the gold surface from the protruding regions of the relief only. Then, the same procedure as in case of the non-patterned surfaces was applied, i.e., exposure of the surface to an aqueous solution of thioglycolate, and subsequently exposure to an EDC-activated PS bead suspension. However, in contrast to the procedure described above, the amount of EDC had to be reduced to yield a total concentration of EDC in the suspension of about 2.5% of the concentration used above. After rinsing and drying, a patterned PS bead surface as shown in FIG. 3 had been formed.

Example 2

Metallization of the Non-Metallic Cores Via Layer-by-Layer Adsorption (LbL)

Figure 4:
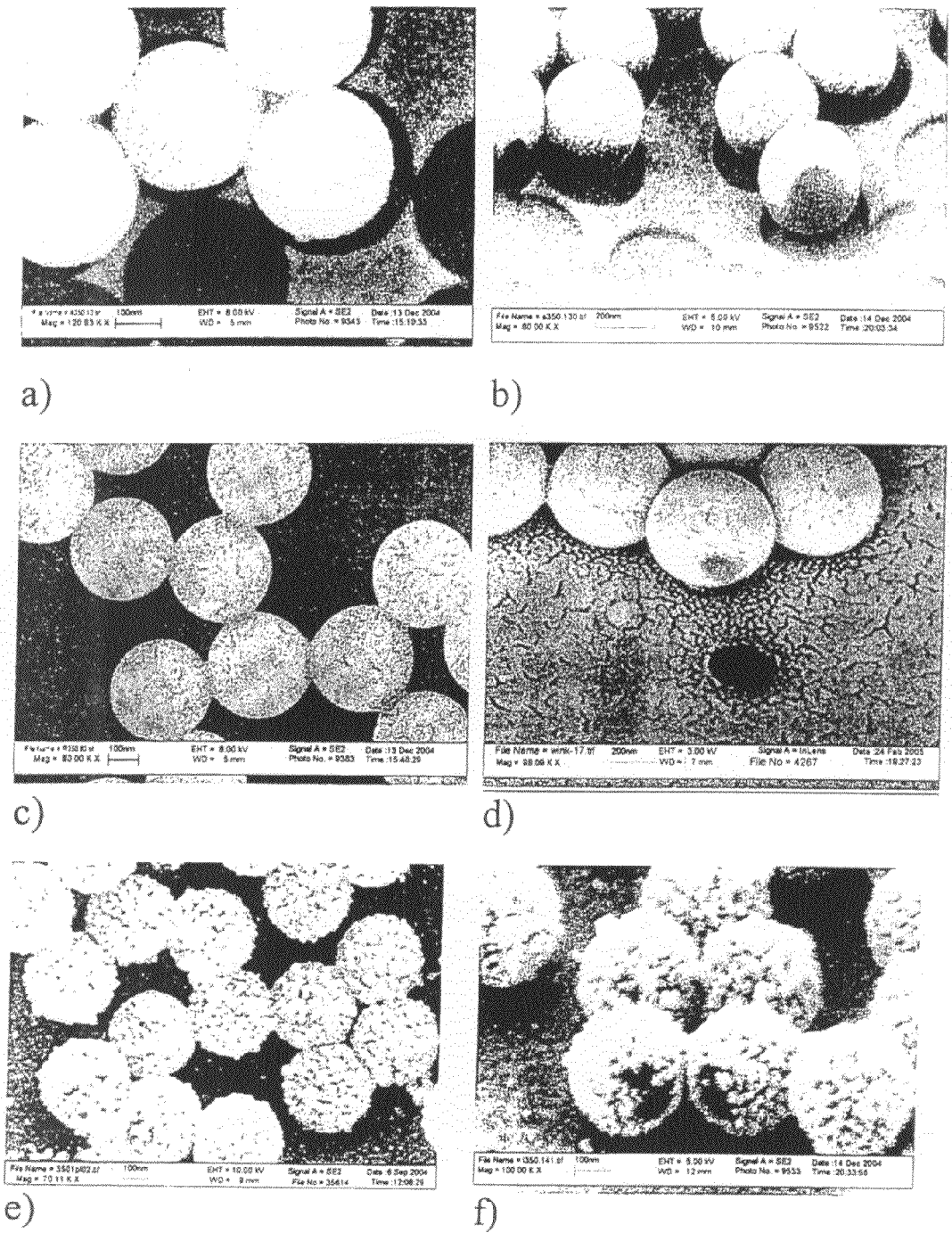
FIGS. 4a to 4f show SEM micrographs of metal-coated non-metallic particle layers prepared by different methods of metallization.

Chip surfaces prepared as outlined in the previous example were covered with a metallic coating in the following manner: Colloidal gold particles with an average diameter of 2-3 nm were prepared by mixing 1 ml of 1% $HAuCl_4 \cdot 3H_2O$(aq) with 100 ml of $H_2O$ under strong stirring for one minute, followed by adding 1 ml of a 1% aqueous $Na_3$ citrate solution. After one minute, 1 ml of 0.075% $NaBH_4$ in 1% aqueous $Na_3$ citrate was added to the solution, which was then further stirred for 5 min. This procedure leads to the formation of citrate stabilized, i.e., negatively charged, colloidal gold particles with an average diameter of 2-3 nm. To adsorb the colloidal gold particles onto the surface covered with PS beads, the surface was first coated with polyelectrolytes to provide a positive surface charge. First, the surface was exposed to 90 µl (here, and in the following: 90 µl per well) of poly(styrene) sulfonic acid (PSS) {1 mg PSS per ml of 0.5 molar $NaCl_{(aq)}$} for 20 min. Then, the surface was rinsed with deionized water. In a second step, the surface was exposed to 90 µl of poly(ethylene imine) (PEI) {2 mg PEI per ml of 0.5 molar $NaCl_{(aq)}$} for another 20 min, and then rinsed with deionized water. This procedure resulted in a positively charged surface, which allowed for the immobilization of negatively charged gold colloids. Accordingly, the surface was subsequently exposed to 90 µl of the previously prepared gold colloid for five hours. After rinsing with deionized water, the surface showed traces of purple color due to the adsorption of the gold colloid. To assure optimum density of colloidal gold particles on the surface, the last step was repeated once. Then, the adsorbed gold particles were grown by an electroless plating step. Thereby, the surface was exposed to a mixture (90 µl per well) of 3.5 ml of 0.1% $HAuCl_4 \cdot 3H_2O$(aq) and 1.5 ml of 0.04 M $NH_2OH$(aq) for 3 min. Then, the surface was rinsed with deionized water and dried in a stream of nitrogen. At this stage of the preparation, the surface showed a deep purple color in reflection when irradiated with white light. FIG. 4a displays scanning electron micrographs of the resulting surface.

Example 3

Metallization of the Non-Metallic Cores Via Sputtering

Alternatively, the surface-adsorbed PS beads were metallized with a thin film of gold by sputtering. By means of a sputter coating system (BAL-TEC, Med020) operated at a base pressure of $5 \cdot 10^{-7}$ mbar and an Ar pressure of $5.1 \cdot 10^{-2}$ mbar, 20 nm of gold were sputtered onto the sample surface. The samples were mounted at a distance of 50 mm from the gold target and sputtered at 30 mA for 67 s. FIG. 4c displays a SEM micrograph of the resulting surface.

Comparative Example 1

Metallization of the Non-Metallic Cores Via Evaporation

For direct comparison with previous work (Himmelhaus and Takei, Sens. Actuators B 2000, 63, pp. 24-30, Takei et al., Opt. Lett. 2002, 27, pp. 342), the surface-immobilized PS beads were coated by evaporation of 20 nm of gold in the same way as described above for the gold coating of the substrate. Thereby, cap-shaped gold shells form on the upper half of the PS beads, as visualized in the SEM micrographs in FIG. 4b.

Comparative Example 2

Chip Fabrication Using Core-Shell Particles

A further comparison was made with core-shell particles consisting of a dielectric core and a metallic shell, as previously published by a number of authors (Oldenburg et al., Chem. Phys. Lett. 1998, 288, pp. 243; Lirtsman et al., Adv. Mater. 2001, 13, pp. 1253, Cassagneau and Caruso, Adv. Mater. 2002, 14, pp. 732; Kaltenpoth et al., Adv. Mater. 2003, 15, pp. 1113).

To obtain a metallic coating for the 350 nm PS beads used in our study, the layer-by-layer adsorption process described by Caruso et al. ("Nano-engineering of inorganic and hydrate hollow spheres by colloidal templating", Science 282: 1111-1114, 1998) for dielectric particles in suspension was applied. In short, 120 ml of an aqueous 350 nm PS bead suspension were mixed with 1 ml PEI solution {2 mg PEI per ml of 0.5 molar $NaCl_{(aq)}$} and 500 µL phosphate buffer (pH 7.4) for 20-30 min. Then, the mixture was centrifuged at 8000 rpm for ten minutes several times to separate the particles from the fluid phase. After each centrifugation step, the clear portion of the fluid was removed via pipetting, followed by adding a proper amount of deionized water to compensate for the loss. In the first centrifugation cycle, the deionized water added to the suspension contained NaCl at a concentration of 0.5 M. Three subsequent centrifugation cycles were performed using pure deionized water. Thereby, an aqueous suspension containing PEI-coated positively charged PS beads was obtained.

For the adsorption of colloidal gold particles (cf. example 2) onto the PEI-coated PS beads, 200 µL of the PS bead suspension were diluted with 300 µL deionized water. Then, 1.5 ml of gold colloid suspension were added. If the purple color of the mixture had vanished after 12 hours, the addition of gold colloid suspension was repeated. After another 12 hours, superfluous gold colloid was removed in three centrifugation cycles.

To form closed metallic shells around the PS beads, 350 µl of 0.1% $HAuCl_4.3H_2O$(aq) and 150 µl 0.04 M $NH_2OH$(aq) were added to the suspension obtained after decoration of the PS beads with the colloidal gold particles. The mixture was shaken for 2-3 minutes, then immediately separated by centrifugation and pipetting. The resulting core-shell particles are displayed in FIG. 7a.

Figure 7:
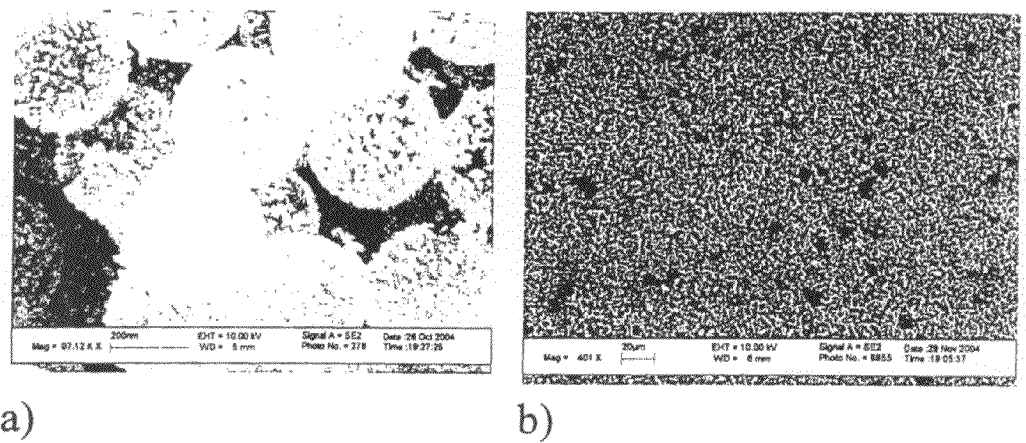
FIGS. 7 a and b show core-shell particles (a) and a chip surfaces formed by core-shell particles prepared according the comparative example 2.

To form a densely packed layer of core-shell particles in the wells of a gold-coated FALCON PS plate (cf. example 1) for direct comparison with the results of example 2, the gold surface was exposed to an aqueous solution of cysteamine for 1 hour and subsequently rinsed with deionized water. Core-shell particles prepared as described above were coated with an additional layer of PSS by mixing 200 µl of core-shell particle suspension with 1 ml PSS solution (cf. example 2) for 30 min. After 30 min, the mixture was ultracentrifuged and separated by pipetting, as described above. Deionized water was added to compensate for the volume loss. This procedure was repeated three times. Then, the core-shell particle suspension was placed onto the cysteamine functionalized gold surfaces for 2 hours. Finally, the suspension was rinsed off and the surfaces were dried in air. A resulting particle layer is shown in FIG. 7b.

Example 4

SEM Micrographs of the Particle Layers Coated with Gold Via the Different Metallization Methods FIGS. 4a and 4b show a chip surface prepared in accordance with EP 0 965 835 A2; FIGS. 4c and 4d show a chip surface prepared according to the present invention by sputtering; FIGS. 4e and 4f show a chip surface prepared according to the present invention by adsorption of colloids and subsequent electroless plating. FIGS. 4b, d and f show the particle layers after removal of some of the neighboring particles with adhesive tape (cf. FIG. 6), so that the apertures which had been formed between the particles become visible. The dark spot on the substrate surface in FIG. 4d indicates where one of the removed particles had been located. Similarly, the former position of removed particles can be seen in FIGS. 4a and b, since the gold was not deposited in regions shadowed by formerly adsorbed particles. In FIG. 4b two particles show contact points, which are surrounded by the metal coating deposited via evaporation to an extent of about $\theta=180°$. The metal coating is not present at that half of the spheres directed towards the substrate surface, since by evaporation only those areas of the surface can be coated which are in direct sight of the evaporation source.

Example 5

Optical Characterization of the Differently Prepared Surfaces

To determine the optical properties of the PS bead surfaces metallized by the different methods described above, the wavelength-dependent extinction of light reflected from the surfaces was measured with a fibre-optical set-up as sketched in FIG. 8a. The reflection fibre probe used for illumination and sampling of the reflected light was placed at a distance of ~10 mm above the surface and oriented perpendicularly to the surface. First, a reference spectrum was recorded from a non-treated surface area of the gold-coated PS substrate, i.e., the inner area of a well only coated with 20 nm of evaporated gold. Then, the wells coated with PS beads and metallized according to the different procedures described above were analyzed at different locations (center of the well and 2-3 spots off the center). Subsequently, the extinction of these layers with respect to the gold reference was calculated.

As a measure for the sensitivity of the different surfaces with respect to adsorption of organic molecules, the surfaces were subsequently exposed to an ethanolic solution of alkanethiols (1 mM octadecanethiol (ODT), 95%; Sigma-Aldrich) for eight hours, then rinsed with pure ethanol (p.a. grade; Sigma-Aldrich) and dried in a stream of nitrogen. Subsequently, extinction spectra were recorded with respect to the reference spectrum. By means of a mechanically controlled 2D translator stage, the same spots as investigated in the first measurement could be analyzed with a precision of <0.1 mm for a total diameter of the detection area of >3 mm.

Figure 9:
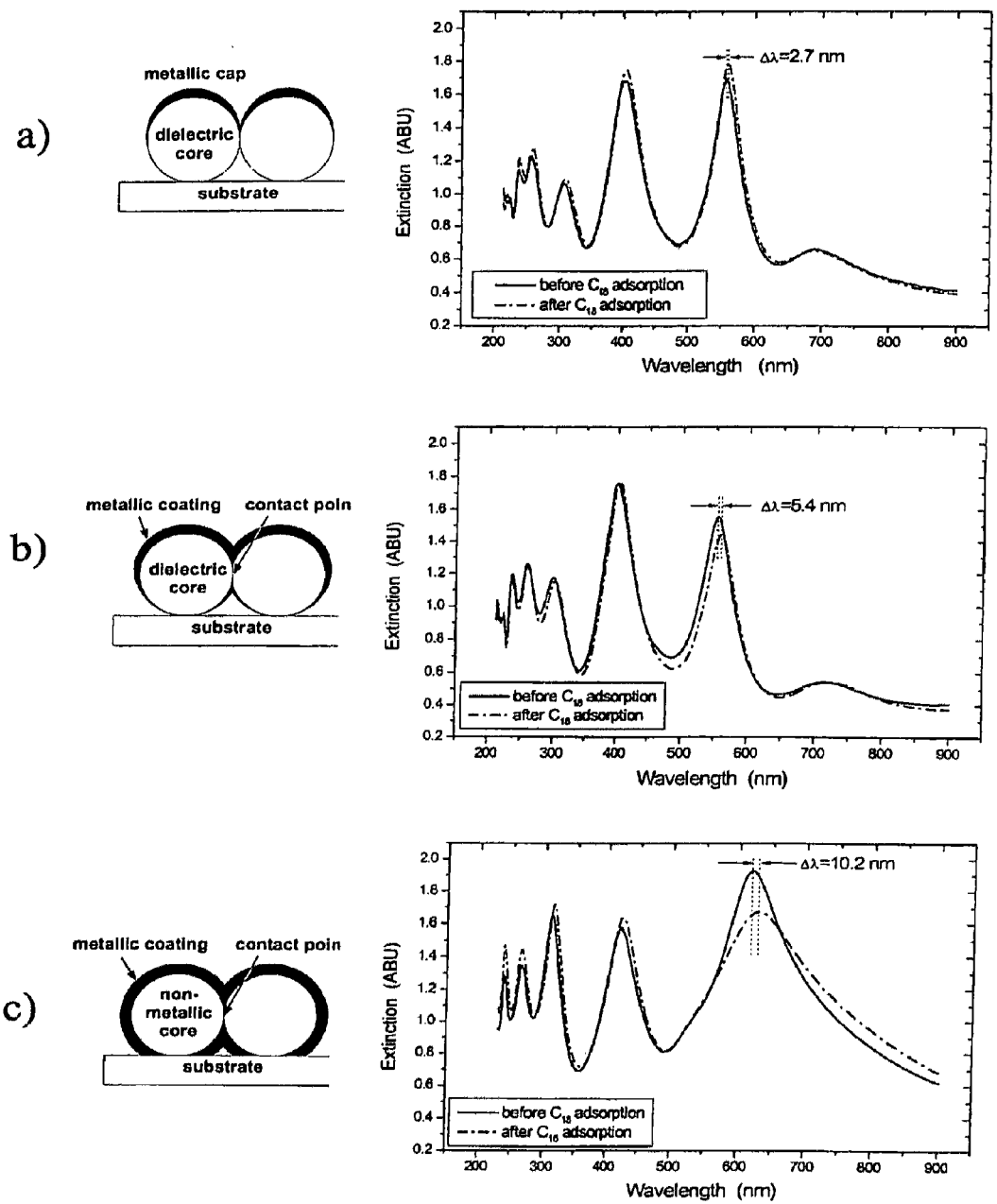
FIG. 9a shows a graphical illustration of the chip surface prepared in accordance with EP 0 965 835 A2 and an extinction spectrum before and after a thiol adsorption experiment on this chip (cf. example 5)
FIG. 9b shows a graphical illustration of the chip surface prepared according to the present invention by sputtering, and an extinction spectrum before and after a thiol adsorption experiment on this chip.
FIG. 9c shows a graphical illustration of the chip surface prepared according to the present invention by colloid adsorption and subsequent electroless plating, and an extinction spectrum before and after a thiol adsorption experiment.

The acquired spectra are displayed in FIG. 9 except for the core-shell particle layer prepared according to comparative example 2, since in this case no pronounced peaks were observable in the entire visible range and the changes in the extinction spectra due to thiol adsorption were negligible. Obviously, the extinction peaks around 560 nm in case of (a) and (b) and 630 nm in case of (c) exhibit a clear shift in response to the adsorption of the thiols. Peak positions and corresponding magnitude of extinction are listed in Table 1. Further, the mean shift in the peak position due to thiol adsorption is given as average over 5 samples. While the changes in the extinction are relatively small, a clear shift in the peak position is observable in particular for chip surfaces with a metallization prepared by the LbL adsorption of colloidal metal particles as described in example 2.

TABLE 1

Peak positions and peak extinctions of UV-vis spectra of chip surfaces before and after adsorption of octadecanethiol. The surfaces were prepared via evaporation, sputtering, and LbL deposition of colloidal metal particles, according to comparative example 1, example 3, and example 2, respectively. The core-shell particles referred to in the last two columns were metallized in solution prior to surface adsorption according to comparative example 2.

| | Evaporated | | Sputtered | | LbL deposition | | Core-Shell Particles | |
| --- | --- | --- | --- | --- | --- | --- | --- | --- |
| Treatment | Peak position (nm) | Peak extinction (ABU) | Peak position (nm) | Peak extinction (ABU) | Peak position (nm) | Peak extinction (ABU) | Peak position (nm) | Peak extinction (ABU) |
| Before C18 adsorption | 556.5 | 1.68 | 553.0 | 1.55 | 617.7 | 1.92 | 837.20 | 1.04 |
| After C18 adsorption | 559.2 | 1.79 | 558.4 | 1.45 | 627.9 | 1.68 | 837.20 | 1.05 |
| After - Before | 2.7 | 0.11 | 5.4 | −0.1 | 10.2 | −0.24 | 0.0 | 0.01 |
| Mean shift (average over 5 samples) | 2.70 nm ± 0.86 nm | | 6.13 nm ± 1.51 nm | | 10.61 nm ± 6.47 nm | | 0.0 (average over 2 samples) | 0.01 (average over 2 samples) |

The invention claimed is:

1. A chip comprising:
   a substrate with at least one, optionally dielectric, surface and, on top of said at least one surface,
   a layer of particles having a non-metallic core and a coating made of a metal or a metal alloy, wherein
   each non-metallic core, on average, has a surface area in direct contact with a surface area of at least one other non-metallic core and/or with the surface of the substrate, and
   the surface area of the non-metallic core in direct contact is not coated by the metal or the metal alloy, while the surface area of the non-metallic core in direct contact is surrounded by the metal or the metal alloy to an extent of 220 degree or more.

2. A chip comprising a substrate with at least one surface and, on top of said at least one surface, a layer of particles having a non-metallic core and a coating made of a metal or a metal alloy, obtainable by
   adsorbing non-metallic particles on said surface of the substrate, and, subsequently,
   sputtering metal clusters or metal alloy clusters on said non-metallic particles, to provide the coating made of a metal or a metal alloy,
   wherein each non-metallic core, on average, has a surface area in direct contact with a surface area of at least one other non-metallic core and/or with the surface of the substrate, and
   the surface area of the non-metallic core in direct contact is not coated by the metal or the metal alloy, while the surface area of the non-metallic core in direct contact is surrounded by the metal or the metal alloy to an extent of 220 degree or more.

3. The chip according to claim 1 or claim 2, wherein the metallic shell uniformly covers the free surface of the non-metallic cores, i.e. the surface not in contact with neither another core nor with the substrate surface.

4. The chip according to claim 1 or claim 2, wherein the non-metallic core is of spherical shape and the metallic coating is also present in the hemisphere of the particles directed towards the substrate surface.

5. The chip according to claim 1 or claim 2, wherein the coating is made of a transition metal or a transition metal alloy.

6. The chip according to claim 1 or claim 2, wherein the substrate consists of a waveguiding material or comprises waveguiding elements.

7. The chip according to claim 1 or claim 2, wherein the layer of the particles is a monolayer with a packing density of at least 35%.

8. The chip according to claim 1 or claim 2, wherein the particles are present in a pattern on the surface,
   wherein the pattern is sufficiently dense for contact point formation.

9. A method for preparing the chip according to claim 1 or claim 2, comprising the steps of
   adsorbing non-metallic particles on said surface of the substrate, and, subsequently,
   sputtering metal clusters or metal alloy clusters on said non-metallic particles, to provide the coating made of a metal or a metal alloy.

10. An optical device for the detection of an analyte, comprising the chip according to claim 1 or claim 2, an optical system for irradiating said chip, and a detection system for detecting the light reflected, transmitted, scattered or diffracted from said chip surface.

11. A method for determining the concentration of an analyte, comprising the steps of
   detecting the light reflected, transmitted, scattered or diffracted from the chip according to claim 1 or claim 2,
   bringing a solution potentially containing one or more analytes in contact with said chip, and
   detecting the light reflected, transmitted, scattered or diffracted from said chip surface during or after exposure to the solution.

12. The chip according to claim 1 or claim 2, wherein
   the surface area of the non-metallic core in direct contact that is not coated by the metal or the metal alloy comprises a single-connected segment of the surface area of the non-metallic core,
   the single-connected segment has a border with the metal or the metal alloy coating the non-metallic core,
   the angle between a first radius from the center of the single-connected segment to one end of the border and a second radius from the center of the single-connected segment to the other end of the border amounts to 220 degrees or more.

13. The chip according to claim 1 or claim 2, wherein a layer composed of a metal or a metal alloy is provided between the substrate and said layer of particles having a non-metallic core and a shell made of a transition metal or a transition metal alloy, and wherein each non-metallic core, on average, forms a metal-surrounded contact point with at least one other non-metallic core.

14. The chip according to claim 13, wherein the layer composed of a metal or a metal alloy is composed of a transition metal, a transition metal alloy, or aluminium.

15. The chip according to claim 13, wherein a non-metallic layer is provided between said layer composed of a transition metal or a transition metal alloy and said layer of particles.

16. The chip according to claim 1 or claim 2, wherein binding agents capable of binding an analyte are immobilized on the surface of the chip.

17. The chip according to claim 16, wherein a plurality of binding agents is immobilized on the surface in such a manner that different locations on the chip surface can be assigned to different binding agents.

18. A chip comprising a substrate with at least one surface and, on top of said at least one surface, a layer of particles having a non-metallic core and a coating made of a metal or a metal alloy, obtainable by
- adsorbing non-metallic particles on said surface of the substrate, and, subsequently,
- sputtering metal clusters or metal alloy clusters on said non-metallic particles, to provide the coating made of a metal or a metal alloy,
- wherein each non-metallic core, on average, has a surface area in direct contact with a surface area of at least one other non-metallic core and/or with the surface of the substrate, and
- the surface area of the non-metallic core in direct contact is not coated by the metal or the metal alloy, while the surface area of the non-metallic core in direct contact is surrounded by the metal or the metal alloy to an extent of 220 degree or more.

* * * * *